United States Patent [19]

Guder et al.

[11] Patent Number: 5,292,669

[45] Date of Patent: Mar. 8, 1994

[54] AGENTS FOR THE DETECTION OF SUBSTRATES WITH HYDROLASE ACTIVITY

[75] Inventors: Hans-Joachim Guder, Weilheim; Werner Güthlein, Mannheim; Wolfgang Weckerle, Grünstadt, all of Fed. Rep. of Germany; Johann Berger; Harvey Buck, both of Indianapolis, Ind.; Rupert Herrmann, Weilheim, Fed. Rep. of Germany

[73] Assignee: Boehringer Mannheim GmbH, Mannheim, Fed. Rep. of Germany

[21] Appl. No.: 927,870

[22] Filed: Aug. 10, 1992

Related U.S. Application Data

[63] Continuation of Ser. No. 422,496, Oct. 17, 1989, abandoned.

[51] Int. Cl.$^5$ .................. C12Q 1/44; C12Q 1/42; C07D 277/82; C07D 233/56
[52] U.S. Cl. .................. 435/18; 435/19; 435/21; 548/161; 548/119; 548/343.5; 536/17.3
[58] Field of Search .................. 435/18, 19, 21; 548/161, 346; 531/19.3

[56] References Cited

U.S. PATENT DOCUMENTS

| 4,089,747 | 5/1978 | Bruschi | 435/28 |
|---|---|---|---|
| 4,279,992 | 7/1981 | Bogusloski et al. | 435/18 |
| 4,407,944 | 10/1983 | Kasahara et al. | 435/18 |
| 4,543,325 | 9/1985 | Albert et al. | 435/18 |
| 4,665,023 | 5/1987 | Deneke et al. | 435/28 |
| 4,698,300 | 10/1987 | Henkel et al. | 435/18 |
| 4,721,670 | 1/1988 | Osada et al. | 435/18 |
| 4,919,890 | 4/1990 | Aria et al. | 422/57 |
| 4,966,855 | 10/1990 | Deneke et al. | 436/66 |

FOREIGN PATENT DOCUMENTS

| 0243066 | 10/1987 | European Pat. Off. | G01N 33/52 |
|---|---|---|---|
| 0291321 | 11/1988 | European Pat. Off. | C12Q 1/34 |
| 0333114 | 9/1989 | European Pat. Off. | G01N 33/52 |
| 0347139 | 12/1989 | European Pat. Off. | C12Q 1/28 |

OTHER PUBLICATIONS

C.A. 85:159962s. Chaudhari et al, "Synthesis and Study of 4-(p-aminophenyl)-thiazoles for in vitro ... ".
C.A. 102:217842k. Fuji Photo, "Analytical Reagents and Multilayered Analytical ... " Japanese Pat. Pub 59-193.353.
C.A. 106:84606v. Hamamaka et al. "Imidazole Derivatives as Chromogenic Agents ... " Japanese Pat. Pub 61-229868.
CA 81(1) 3072h, Rogers et al, "Control of Modes of Intramolecular Imidazole ... ".
CA 75(15) 97654N; Bornowski, H.; "Imidazole Derivatives".
CA 102(5) 46224d; Froehler et al; "1-Methyl-2-(2-hydroxyphenyl) imidazole".
CA 105(25) 227239v; Froehler et al.; "Intermediates from Oligonucleotide Synthesis."

Primary Examiner—Michael G. Wityshyn
Assistant Examiner—T. J. Reardon
Attorney, Agent, or Firm—Felfe & Lynch

[57] ABSTRACT

A method of detecting hydrolase activity using as substrates the compounds of the formula

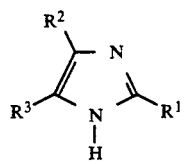

wherein each of $R^1$, $R^2$ and $R^3$ is $C_1$–$C_4$ alkyl, or phenyl optionally substituted in the meta- or para- position by $C_1$–$C_6$ alkyl, $C_1$–$C_6$ alkoxy or mono- or di-($C_1$–$C_6$)-alkylamino, or optionally substituted by an O–X group in which X is a glycosyl, phosphate or acyl moiety of a natural substrate of the corresponding glycosidase, phosphatase or esterase.

26 Claims, 1 Drawing Sheet

AGENTS FOR THE DETECTION OF SUBSTRATES WITH HYDROLASE ACTIVITY

This is a continuation of application Ser. No. 422,496 filed on Oct. 17, 1989 now abandoned.

FIELD OF THE INVENTION

The present invention is concerned with a process for the detection of substances with hydrolase activity and with an agent suitable for carrying out the process, as well as with new hydrolase substrates and processes for the preparation thereof.

BACKGROUND AND PRIOR ART

Hydrolases are enzymes which have recently achieved great importance. On the one hand, they play an important role in the metabolism of plants and animals and also of humans. If the concentration of a hydrolase in one of these biological systems deviates from the concentration normally present therein, then this can be the cause of a disease. Therefore, it is .2 task of clinical diagnosis, in the case of the presence of a disease, to ascertain, by determination of the concentration of a hydrolase in body fluids, possible deviations from the normal value. This preferably takes place via the determination of the hydrolase activity by means of an indicator reaction. For this purpose, the sample to be investigated is mixed with a substrate for the hydrolase in question. The amount of product formed from the substrate is a measure for the hydrolase concentration present.

On the other hand, hydrolases are used ever more frequently as enzymes for labeling immunologically active compounds. $\beta$-Galactosidase is hereby especially widely used for the labelling of, for example, antibodies in immunological tests (see Annals of Clinical Biochemistry, 16, 221/1979). Tests of this kind serve to determine the content of an immunologically active analyte in a sample. They are so constructed that the concentration of the analyte is determined via an appropriate immune component which carries covalently bound $\beta$-galactosidase as label. The test is so constructed that the concentration of the immune partner is directly dependent upon the concentration of the analyte to be determined. The concentration of the labelled immune component is also made visible via an indicator reaction, in which the immune component labelled with $\beta$-galactosidase is reacted with a substrate for $\beta$-galactosidase.

The amount of product formed is proportional to the concentration of the immune component. By comparison with the values of a calibration curve, which is produced with the help of samples with known analyte concentration, an unknown analyte concentration in a sample can be determined.

Hydrolases are also used as enzymes for labelling nucleic acids in processes for the detection of nucleic acids. Such a process which uses $\beta$-galactosidase as enzyme label is described in Federal Republic of Germany Patent Specification No. 29 15 082. Here, too, the amount of label is determined in an indicator reaction.

Furthermore, hydrolases are used as reagents in research. Here, too, it is important to be able to determine the concentration of the enzymes exactly and quickly. In general, for this purpose, there are used methods which are similar to those used in clinical diagnosis.

The substrate used is generally a chemical compound which is soluble in the sample liquid. In the case of the reaction with the hydrolase, a product is formed which differs in one of its characteristics, for example a characteristic light absorption, a light emission (fluorescence) or the like, from the substrate and can thereby be determined.

In the case of test processes on immunologically active substances, a differentiation is made between two technical embodiments. In the case of a frequently used embodiment, the detection reaction takes place in a cuvette such as is generally used for photometric investigations. The evaluation of the indicator reaction is then carried out by measurement of the absorption, emission or radio-activity in an appropriate apparatus.

In the case of another embodiment, the reactions take place in one or more fleece or films which are parts of a test carrier, the necessary reagents being applied to these fleece or films. The amount of product which is liberated by the hydrolase activity from the hydrolase substrate during the indicator reaction can then be determined directly in such a fleece or film. An advantage of this embodiment is that it is possible to work with only a single solution, the liquid sample, which considerably simplifies the carrying out of the process. The amount of product formed can be detected especially simply by measurement of the light absorption at a particular wavelength.

Substrates suitable for this purpose include the phenyl-sulphophthaleinyl-$\beta$-D-galactosides and derivatives thereof, which are described in European Patent Specification No. 01 46 866, from which phenylsulphophthalein derivatives are liberated by reaction with $\beta$-D-galactosidase. Whereas the substrate has a yellow color, the product is red colored. Thus, during the indicator reaction, a gradual color change from yellow via orange to red takes place. The color change can only be assessed very inaccurately with the naked eye so that an appropriate photometer must be used for the measurement.

The resorufin-$\beta$-D-glycosides described in European Patent Specification No. 0 156 347 are also substrates in which case the reaction with a glycosidase causes a color change from yellow to red to take place. It has been ascertained that in the transitional region between yellow and red, especially in the case of low $\beta$-glycosidase activities, the visual evaluation leads to subjective results, for which reason apparatus are here also used for the evaluation. However, these apparatus are relatively complicated and, therefore, expensive. The resorufin glycosides are not very suitable as substrates for use in test carriers since resorufin formed from them bleeds out, because of its water solubility.

Hydrolase substrates such as, for example methylumbelliferone galactoside, in which hydrolysis causes only a change of the fluoresence properties, are also unsuitable for a visual evaluation. Methylumbelliferone galactoside also gives rise to a substance, which easily bleeds out of the test strips.

Furthermore, processes for the detection of substances with hydrolase activity have been suggested in which uncolored hydrolase substrates are used which, in the case of reaction with a hydrolase, are converted into colored products. Consequently, in the case of these detection reactions, the formation of a color is to be assessed rather than a color change. This can take place in a simple way by comparison of the color intensity with a color shade of a color scale. Even color blind persons can evaluate such a test.

5-Bromo-4-chloro-3-indolyl-β-galactoside is such a substrate. After cleavage and oxidation, this substrate gives a colored material which does not bleed out on test carriers. However, the substrate itself is not very water-soluble. Thus, a test constructed thereon is not very suitable for a rapid visual evaluation. The mechanism which leads to the color formation is the oxidative dimerisation of two 5-bromo-4-chloroindolyl units to give an indigo colored material. Thus, for the formation of one molecule of colored material, two enzymatic cleavages are necessary. Thus, only half of the theoretically possible sensitivity is achieved.

In Biochem. Z., 333, 209/1960, compounds were suggested as substrates in which the hydrolysis thereof liberates phenols. However, these easily bleed out of the test carrier. In the case of nitrophenol, during the indicator reaction, a more or less intensive yellow coloration develops. The visual evaluation in the range of small concentrations is very unfavorable at the wavelengths of the nitrophenols.

For improving visibility, in an additional reaction, the liberated phenols are coupled oxidatively with 4-aminoantipyrine or methylbenzothiazolinone hydrazone (Anal. Biochem., 40, 281/1971) or with diazonium salts to give azo dyes (see, for example, Histochemie, 37, 89/1973). Some of these dyes are admittedly suitable for use in test carriers since they do not bleed out very easily. However, the use of these coupling reactions is disadvantageous for other reasons. Thus, for carrying out the test on a fleece or film, all the reagents necessary for this additional reaction must also be applied to a fleece or introduced into a film. The large number of reagents, for example coupling partners, make the carrying out of the test complicated and result in numerous disadvantages and difficulties. Thus, in individual cases, care must be taken that the reagents do not already react prematurely with one another or non-specifically with other components of the sample solution etc. Thus, aminoantipyrine or methylbenzothiazolinone hydrazone can also react with components in, for example, investigated urine and thus falsify the measurement. Other coupling components, for example diazonium salts, considerably impair the storage stability. In choosing reagents, it should also be required that they not themselves have an inherent color, or other disadvantages.

Bleeding phenomena which occur in the case of some of the colored materials formed on test carriers will, for example, result in color intensity not being equal in all points of the fleece or film. This results in disadvantages in the evaluation. Since, for example, the measurement values are falsified.

Therefore, there is a need for hydrolase substrates in which the above-mentioned disadvantages are avoided and with the help of which substances with hydrolase activity can also be detected on test carriers in a simple, rapid and dependable manner.

It is an object of the present invention to satisfy this need.

SUMMARY OF THE INVENTION

Thus, according to the present invention, there are provided compounds of the general formula (I)

wherein: Z is an oxygen or sulphur atom or an radical; $R^1$, $R^2$ and $R^3$, which can be the same or different, are hydrogen atoms or alkyl, aralkyl or aromatic radicals; and $R^4$ is a hydrogen atom or an alkyl radical; and in which one or more of the radicals $R^1$, $R^2$ and $R^3$ is an aromatic radical substituted by an —O—X group, in which X is a glycosyl, phosphate or acyl radical.

The alkyl radicals $R^1$, $R^2$, $R^3$ and $R^4$ preferably contain up to 6 carbon atoms. Alkyl radicals with up to 4 carbon atoms are especially preferred and the methyl radical is quite especially preferred.

As aralkyl radicals $R^1$, $R^2$ and $R^3$, there are preferred aralkyl radicals containing 7 to 11 carbon atoms, the benzyl radical being especially preferred.

An aromatic radical in the meaning of $R^1$, $R^2$ and $R^3$ can be unsubstituted or substituted and preferably contains 6 to 12 carbon atoms. As unsubstituted radical, the phenyl and naphthyl radical are preferred. Further possible radicals include, for example, heteroaryl radicals, for example furyl or pyridyl radicals.

Substituted aromatic radicals are preferably the phenyl and naphthyl radicals in which one or more hydrogen atoms are replaced by halogen, hydroxyl, alkoxy, alkyl, amino, mono- or dialkylamino, carboxyl, carbamoyl, alkoxycarbonyl, alkylcarbonyl, formyl or sulpho radicals or the group —O—X. An aromatic radical can also simultaneously carry various types of these substituents. As halogen, there is preferred chlorine, bromine or iodine, and especially chlorine.

Alkyl groups of the aromatic radical and alkyl moieties in the individual substituents of the aromatic radical preferably contain up to 6 and especially up to 4 carbon atoms and can, in turn, be unsubstituted or substituted. Especially preferred is the methyl group. Preferred substituents of the alkyl radicals include halogen, hydroxyl, alkoxy, carboxyl, sulpho, phosphono and morpholino.

The carboxyl, sulpho and phosphono groups can also be esterified, preferably with methanol or ethanol.

The preferred substitution positions in the aromatic radicals are the meta- and para-positions.

Especially preferred compounds of general formula (I) are those in which one of the radicals $R^1$, $R^2$ and $R^3$ is a phenyl radical substituted by —O—X group and another or both other radicals are aromatic radicals which have one or more electron-donating substituents, for example hydroxyl groups, substituted or unsubstituted amino groups, alkoxy radicals or the like. The preferred substitution position for the electron-donating substituents is the para-position. Preferred substituents of the amino groups are alkyl radicals containing up to 4 carbon atoms and especially preferably the methyl and ethyl radicals, or acyl radicals containing up to 6 carbon atoms, preferably the acetyl radical. Disubstituted amino groups are preferred.

The aromatic radical which carries the —O—X group can also be substituted, preferred substituents being alkoxy and alkyl radicals, the methoxy radical being especially preferred. As aromatic radical in the meaning of the radicals $R^1$, $R^2$ and $R^3$ which does not carry an —O—X group, there is preferred the 4-dimethylaminophenyl, 9-julolidino or 4-($C_1$-$C_4$-alkoxy)-phenyl radical and especially preferably the 4-methoxyphenyl radical, as well as the 6-N-methyl-1,2,3,4-tetrahydroquinolino radical, in which the methyl substituents can carry carboxyl, phosphono or sulpho groups.

Glycosyl radicals of the group X are mono-, oligo- and polysaccharide radicals of the hexosepyranoside series. Preferred are monosaccharide residues, for example the glucosyl or galactosyl radical, but also the glucosamine radical which, if desired, can be acylated and preferably N-acetylated. The binding of the glycoside radical can be α- or β-glycosidic.

Acyl radicals of the group X preferably contain up to 20 carbon atoms and can be saturated or unsaturated and straight-chained or branched, the acetyl radical being especially preferred.

The acyl radicals also include the aminoacyl radicals. Preferred as aminoacyl radicals are the residues of naturally occurring α-L-amino acids bound via the carboxyl function. The free polar residues of the amino acids, for example the amino functions, can thereby be protected by appropriate protective groups. Such an amino acid residue is, for example, the alanyl radical which carries a tosyl radical on the amino function.

The phosphate residue is the —$PO_3H_2$ radical and the salts thereof. As cations in the salts, there can be used all positively charged ions, the alkali metal, alkaline earth metal and ammonium ions being preferred and the sodium, potassium, magnesium and calcium ions being especially preferred.

In the compounds of general formula (I), all the radicals $R^1$, $R^2$ and $R^3$ can signify an aromatic radical substituted by the group —O—X. However, compounds of general formula (I) are preferred in which at most two and quite especially preferably only one of the radicals $R^1$, $R^2$ and $R^3$ represents such an aromatic radical.

When Z is an oxygen or sulphur atom, then compounds thereof are preferred in which $R^1$ and $R^2$ are aromatic radicals but $R^3$ is not a hydrogen atom.

When Z is an oxygen or sulphur atom, compounds of general formula (I) are especially preferred in which only one of the radicals $R^1$ and $R^2$ is an aromatic radical substituted by the group —O—X. As second and third radicals of the group $R^1$, $R^2$ and $R^3$, aromatic radicals both carrying a hydroxyl group and aromatic radicals both carrying an amino group are not preferred. However, compounds in which one of $R^1$, $R^2$ and $R^3$ is an aromatic radical carrying a hydroxyl group and another of $R^1$, $R^2$ and $R^3$ is an aromatic radical carrying an amino group are not in this "not preferred" category.

When Z is an group, compounds of general formula (I) are especially preferred in which only one of the radicals $R^1$, $R^2$ and $R^3$ is an aromatic radical substituted by an —O—X group. If $R^1$ is this radical, then compounds are preferred in which $R^2$ and $R^3$ are not both aromatic radicals carrying a hydroxyl group or are not both aromatic radicals carrying an amino group. If $R^2$ or $R^3$ is an aromatic radical substituted by an —O—X group, then compounds are preferred in which $R^1$ and the other of $R^2$ and $R^3$ are not both aromatic radicals carrying a hydroxyl group or are not both aromatic radicals carrying an amino group.

DETAILED DESCRIPTION OF PREFERRED EMBODIMENTS

The compounds of general formula (I) are new compounds. They can be prepared by reacting a compound of the general formula (II)

wherein Z, $R^1$, $R^2$, $R^3$ and $R^4$ have the above-given meanings but in which one or more of the radicals $R^1$, $R^2$ and $R^3$ is a radical substituted by a hydroxyl group instead of by an —O—X group, with a compound of the general formula (III)

in which X has the above-given meaning and Y is a reactive group.

For the case in which X is a glycosyl radical, for this purpose, processes can be used which are known for similar compounds from carbohydrate chemistry.

For this purpose, compounds of general formula (II) are reacted with an activated sugar of general formula (III). Compounds have thereby proved to be especially suitable in which Y is a nucleophilic group which is easily split off, for example a halogen atom, especially a chlorine or bromine atom, or a sulphonyloxy radical, especially a toluenesulphonyloxy or methanesulphonyloxy radical. It has thereby proved to be advantageous to protect hydroxyl or amino groups during the reaction by means of appropriate protective groups. However, the hydroxyl group which is to be converted into an —O—X group should not carry a protective group.

For the case in which X is an acyl radical, processes can be used such as are generally known for the preparation of esters from alcohols, as well as special phenols, by reaction with organic carboxylic acids. Before the esterification, functional groups of the amino acids are advantageously masked by means of appropriate protective groups. After the reaction, the protective groups can be split off again. The reactive group Y is preferably a nucleophilic group which is easily split off. Halogen, alcoholate and carboxylate are thereby especially advantageous.

For the preparation of compounds of general formula (I), in which X is a phosphate residue, compounds of general formula (III) are especially appropriate in which X is a —$POW_2$ or —$PW_4$ group in which W is a group which is easily removed, especially an alcoholate containing up to 4 carbon atoms or chloride, bromide or iodide and Y is a halide, preferably a chloride, bromide or iodide, or an alcoholate, phosphorus oxychloride being especially preferred as a compound of the general formula X-Y. With the exception of the hydroxyl group to be converted into an —O—X group, free hydroxyl and amino groups are advantageously masked by protective groups which can be split off after the reaction. Compounds in which X is a —$POW_2$ or —$PW_4$ group can be converted into the phosphates by hydrolysis in known manner, The salts of the phosphates can be prepared from the free acids in known manner, for example by ion exchange.

The compounds of general formulae (II) and (III) are known compounds or can be prepared analogously to known processes of organic synthesis. In particular, triarylimidazoles are known from Federal Republic of Germany Patent Specification No. 27 35 690. European Patent Specifications Nos. 0,161,436 and 0,167,973 also describe compounds of general formula (II). The use extends to the detection of hydroperoxide.

The compounds of general formula (I) according to the present invention can also be prepared, for example, in known manner either a) for the case in which Z is an radical and X is a glycosyl radical, by condensing an α-diketone of the general formula $$R^2-CO-CO-R^3 \qquad (IV)$$

in which $R^2$ and $R^3$ have the above-given meanings, with an aldehyde of the general formula $$R^1-CHO \qquad (V)$$

in which $R^1$ has the above-given meaning and with ammonia or an amine of the general formula $$R^4-NH_2 \qquad (VI)$$

in which $R^4$ has the above-given meaning, in glacial acetic acid; or b) for the case that Z is an group and X is a glycosyl radical, an a-ketoxime of the general formula in which $R^2$ and $R^3$ have the above-given meanings, is reacted with an aldehyde of general formula (V) and ammonia or an amine of general formula (VI) to give a compound of the general formula in which $R^1$, $R^2$ and $R^3$ have the above-given meanings, and this compound is reduced; or c) for the case that Z is an group and X is a glycosyl radical, an a-haloketone of the general formula $$R^2-CO-CHR^3Hal \qquad (VIII)$$

in which $R^2$ and $R^3$ have the above-given meanings and Hal is a fluorine, chlorine or bromine atom, is reacted in an alkaline medium with an amidine of the general formula in which $R^1$ has the above-given meaning; or d) for the case that Z is an oxygen atom or an group, a compound of the general formula in which $R^1$, $R^2$ and $R^3$ have the above-given meanings, is reacted with a Lewis acid or pentasulphide; or e) for the case that Z is an oxygen atom, a compound of the general formula in which $R^1$, $R^2$ and $R^3$ have the above-given meanings, is reacted with ammonium acetate in glacial acetic acid; or f) for the case that Z is a sulphur atom and X is a glycosyl radical, a thioamide of the general formula $$R^1-CS-NH_2 \qquad (XII)$$

in which $R^1$ has the above-given meaning, is reacted with an α-haloketone of general formula (VIII), in which $R^2$ and $R^3$ have the above-given meanings and Hal is a fluorine, chlorine or bromine atom; and subsequently, if necessary, the compounds obtained are converted into compounds of general formula (I), and also appropriate bases are converted into salts or salts into bases.

In these processes, reactive functional groups possibly present on which no reaction is to take place are protected by known protective groups which can subsequently be split off.

The conversion of compounds obtained according to processes a) to f) into compounds of general formula (I) can take place, for example, by catalytic hydrogenation (nitro to amino), splitting off of protective groups by hydrogenation in the presence of palladium/charcoal (O-benzyl to hydroxyl), hydrogenation of heterocycles (furanyl to tetrahydrofuranyl), cleavage of heterocycles by hydrogenation (tetrahydrofuranyl to 4-hydroxybutyl) and reductive alkylation of amines (amines to dialkylamines).

By the reaction of 4-amino compounds of general formula (I) with halomethane- or 2-ethane-carboxylic acids,-sulphonic acids, as well as-phosphonic acids or the salts thereof in dimethylformamide, there are obtained the corresponding N-alkylaminomethane or 2-ethane acid radicals.

The reduction of N-oxides of general formula (VIIA) can take place, for example, with zinc/acetic acid or catalytically activated hydrogen.

The synthesis of compounds of general formula (I) can also take place according to the methods described in J. Org. Chem., 2, 319/1937; Z. Chem., 10, 431/1970 and 11, 10/1971.

Surprisingly, the new compounds of general formula (I) according to the present invention are outstandingly suitable as hydrolase substrates. They are water-soluble, colorless and stable so long as they do not come into contact with a hydrolase.

If an exceptionally good water-solubility is desired, then it is advantageous to use compounds of general formula (I) in which are present one or more polar residues, for example carboxyl, sulpho or phosphono groups.

The solubility of the compounds of general formula (I) can also be achieved by lowering the polarity of the reaction medium, for example by the addition of organic solvents, such as alcohols or dimethyl sulphoxide, or of detergents.

As hydrolase substrates in the process according to the present invention, there can also be used those compounds of general formula (I) in which the X moiety of the molecule is a molecule moiety of the natural substrate of the corresponding hydrolase. Thus, for example, as $\beta$-galactoside substrates, there can be used compounds of general formula (I) in which X is a $\beta$-galactosyl radical, as esterase substrates those in which X is an acyl radical and, as phosphatase substrates, compounds of general formula (I) in which X is a phosphate residue.

The present invention also provides a process for the detection of substances with hydrolase activity in a sample by mixing the sample with a hydrolase substrate, as well as with an oxidation agent and evaluation of the resultant color intensity, wherein a compound of general formula (I) is used as hydrolase substrate.

Substances with hydrolase activity are substances which can cleave chemical compounds into two products with the consumption of water. To these belong naturally occurring and synthetically produced hydrolases of the enzyme main class 3. The process according to the present invention has proved to be especially useful for the detection of glycosidases, preferably of glucosidases and galactosidases, esterases, preferably lipases and phosphatases, especially preferably alkaline phosphatase or hog's liver esterase.

However, by substances with hydrolase activity are also to be understood compounds of these hydrolases with other chemical compounds, for example immunologically active compounds or nucleic acids. To the immunologically active compounds belong, for example, haptens, antigens, antibodies and immune complexes. However, there equally apply fragments of antibodies, such as Fab or F(ab')$_2$ fragments. These compounds of the hydrolases with immunologically active compounds are often referred to as hydrolase conjugates. The hydrolase thereby serves for labelling the immunologically active compound. The process according to the present invention is especially useful for the detection of immunologically active compounds with $\beta$-galactosidase or $\beta$-glucosidase, as well as with alkaline or acidic phosphatase as label.

A compound is designated a hydrolase substrate when it is reacted by the substance in question with hydrolase activity. Two products are formed from the substrate, with the take up of water. The reaction thereby obeys the known laws of enzyme kinetics. It is a prerequisite that the substrate is, at least to a greater extent, soluble in the solution containing the substance with hydrolase activity.

By a sample is preferably to be understood a solid or liquid sample.

In the case of a solid sample, a differentiation can be made between a soluble and a substantially insoluble sample.

A soluble sample is advantageously converted into a liquid sample for the detection.

By a substantially insoluble sample is preferably to be understood a solid material on the outer or inner surface of which is bound a substance with hydrolase activity. The nature of the binding is not of importance for the process according to the present invention. This binding can be, for example, not only covalent but also ionic or adsorptive or also biospecific. Biospecific bindings are bindings between biological binding components, for example the binding between substances acting as antigen or hapten and antibodies, biotin and avidin or streptavidin, complementary nucleic acids and the like.

By a liquid sample in which the substances with hydrolase activity are to be detected are to be understood essentially aqueous solutions. These solutions can be, for example, solutions of a hydrolase in water. To these solutions are often added admixtures, for example salts, detergents and the like, for example for increasing the storage stability. The process according to the present invention can also be applied to such solutions. The liquid sample can also be a body fluid or a liquid obtained therefrom by the addition or removal of components. To these belong, for example, blood, blood plasma, serum and urine.

The liquid sample can preferably also be a liquid which results in the course of immunological test processes. These are described, for example, in Annals of Clinical Biochemistry, 16, 221/1979, as well as their advantageous further developments which are known to the expert in the field of immunoassays. In such liquids, there can also be detected substances with hydrolase activity by means of the process according to the present invention. These solutions mostly contain buffer substances, stabilizers, wetting agents and the like which, however, do not decisively disturb the detection.

The concentration of substances with hydrolase activity can be advantageously determined in a range of from $10^{-6}$ to $10^{-15}$ mole/liter and preferably of from $10^{-6}$ to $10^{-12}$ mole/liter.

The process can be used for sample solutions in which the pH value is from 5 to 11 and preferably of from 6 to 10. The optimum pH value at which the process is carried out depends upon the hydrolase used. For the rapid carrying out of the process, it is advantageous to work close to the pH value at which the hydrolase displays an activity maximum. Outside of this range, non-enzymatic hydrolysis or inactivation of the hydrolase can markedly take place.

The detection reaction is preferably carried out in an absorbent or swellable carrier. Such carriers are, for example, fleece or films, fleece being preferred. By fleece are to be understood paper-like materials made up of fibers. As fiber materials, there are preferably used cellulose, synthetic resins or mixtures thereof. Sponge-like and/or porous carriers can also be used.

However, the reaction can also be carried out in a vessel of any desired shape, for example a cuvette or also on a microtiter plate. When the course of the reaction is to be monitored by means of an absorption photometer, those compounds of general formula (I) are especially preferred in which products are formed which are soluble in the reaction medium. One possibility is the use of compounds of general formula (I) which, depending upon the polarity of the reaction medium, have one or more polar groups, for example a carboxyl or sulpho group, and the radicals of which do not have strongly lipophilic properties. A further possibility for the detection of substances with hydrolase activity in solution is the addition of solvents lowering the polarity of the reaction medium, for example organic solvents. Insofar as the disadvantage of these additional components can be taken into account, the solubility of the hydrolysis products is increased.

For the development of a color during the indicator reaction, the presence of an oxidation agent is necessary. As oxidation agents, there can be used those substances or substance mixtures, the oxidation potential of which lies above the value for the liberated compound of general formula (II). Potassium ferricyanide, perborate/peroxidase, peroxide/peroxidase, tetrazolium salts and oxygen/bilirubin oxidase have proved to be especially advantageous.

For carrying out the process according to the present invention, the sample is mixed with at least one and preferably one compound of general formula (I) as hydrolase substrate and an oxidation agent.

The mixing of the sample with the hydrolase substrate can take place in different ways.

The mixing of the sample with the hydrolase substrate and the oxidation agent can take place simultaneously or successively.

In the case of a liquid sample, for example of a solution of the substance with hydrolase activity, the hydrolase substrate or the oxidation agent can be added to the sample in the form of a solid material, for example of a powder, a tablet, a lyophilisate or the like, or in the form of a solution.

If the detection reaction takes place in an absorbent or swellable carrier, then it has proved to be especially advantageous to apply the sample to a carrier on which is impregnated the hydrolase substrate, as well as possibly the oxidation agent and additive materials. For the impregnation, there is prepared a solution of the said materials and the carrier material is then impregnated therewith. The impregnated carrier material is subsequently dried.

For the case in which the carrier is a film, the hydrolase substrate, as well as possibly oxidation agent and additive materials, are already incorporated into the film during the production thereof.

If the oxidation agent is not present together with the hydrolase substrate, the oxidation agent is mixed with the sample before or after mixing the sample with the hydrolase substrate.

If the detection reaction takes place in a vessel, then it has proved to be especially advantageous to use the hydrolase substrate in solid form or as solution, possibly mixed with the oxidation agent and the additive materials. Here, too, the oxidation agent and the additive materials can be added separately.

In the case of a solid sample, for example when the substance with hydrolase activity is bound to a carrier material, it is advantageous to add the hydrolase substrate and/or the oxidation agent to the sample in the form of a solution. However, it is, for example, also possible first to mix the components and then to add a liquid for the preparation of a solution.

For the success of the detection process, it is important that the hydrolase substrate can so enter into contact with the substance with hydrolase activity present in the sample that the enzyme reaction can take place.

During the indicator reaction, a strong color is formed which, depending upon the nature of the substitution, extends from red to blue. The color intensity can be measured by known processes with photometers and especially with reflection photometers. For this purpose, light is beamed in with a wavelength which the product of the indicator reaction can absorb. A wavelength of from 500 to 700 nm is preferred and especially one of from 520 to 680 nm.

The color intensity is compared with the values of a calibration curve which is obtained by measurement of the values for samples with known concentrations of substances with hydrolase activity and each intensity is associated with a particular concentration. This comparison is advantageously carried out with the help of a computer.

Since a color development rather than a color change must be observed, the evaluation is also possible with the human eye. This has the advantage that an apparatus does not have to be used. Thus, possible sources of error, such as an incorrect use of the apparatus and the like, also do not arise.

The process according to the present invention can be used for the qualitative and also for the quantitative detection of substances with hydrolase activity. For the qualitative evaluation, it is observed whether a coloration has been produced. For the quantitative determination, at a fixed point of time, the color is compared visually with a color chart which associates each color with a particular concentration.

In the case of the use of hydrolase substrates according to the present invention, particularly intensively colored compounds are formed. Depending upon the nature of the substitution, there can be obtained compounds with colors from blue to red. A large breadth of use results.

The process according to the present invention can be used especially on test strips with great advantage. The advantages are, for example, that the process is simple and inexpensive and, nevertheless, provides dependable results. The process is simple in that, for example, evaluation can also be made visually so that expensive apparatus is not necessary. It is especially dependable since it does not result in bleeding phenomena on the test carriers, which is of great advantage.

By test carriers are understood agents for the detection of substances by carrying out a test. Usually, they consist mainly of a base plate or foil on which are applied the reagents necessary for the test, mostly by means of fleece or films.

In the process according to the present invention, there are preferably used no further coupling components, for example diazonium salts, since these result in side reactions or losses of stability. Only a compound of general formula (I) participates in the color formation. In this way, the disadvantages which occur in the case of condensation reactions between two compounds and which are present in the case of compounds of the indole type are avoided.

In the case of immunological test processes, there are also obtained samples especially of hydrolase conjugates which are to be investigated for their content of substances with hydrolase activity.

Therefore, the process according to the present invention can find special use for the detection of a substance with hydrolase activity in immunological processes for the detection of an analyte. Such processes are known to the expert in the field of immunoassays (see, for example, Annals of Clinical Chemistry, 16, 221/1979). These processes are modified in that the detection of hydrolase-labelled immunologically active compounds necessary therein is carried out by means of the process according to the present invention.

For the case in which the analyte is an antigen or hapten, the following processes have proved to be useful:

The sample solution containing the analyte is mixed with an excess of conjugate of an antibody against the analyte and a hydrolase. An immune complex is formed of analyte and conjugate. The excess of conjugate is bound by immune reaction to a carrier to which is bound an excess of analyte or of an analyte-analogous compound. The solution containing the conjugate of hydrolase and immune complex is separated from the carrier and treated by the process according to the present invention. There is obtained an experimental result for the hydrolase conjugate from which can be deduced the presence or the amount of the analyte. Another possibility is the detection of the conjugate of hydrolase and antibody bound to the carrier. This is also possible with the process according to the present invention.

The sample solution containing the analyte is mixed with an excess of conjugate of an antibody against the analyte and a hydrolase, an immune complex of analyte and conjugate being formed. The excess of conjugate is bound by immune reaction to a carrier-to which is bound an excess of a further antibody against the analyte. The solution containing the excess of conjugate of hydrolase and antibody is separated from the carrier and, according to the process of the present invention, there is detected either the conjugate of immune complex and hydrolase bound to the carrier or the conjugate of antibody and hydrolase contained in the solution.

The sample solution containing the analyte is mixed with a known amount of conjugate of analyte or analyte analog and a hydrolase. The mixture is applied to a carrier to which is bound a known amount in deficiency of an antibody against the analyte and the analyte analog, referred to the sum of analyte and conjugate. A part of the analyte and of the conjugate is bound to the carrier. According to the process of the present invention, after separation of the solution, there can be detected either the conjugate bound to the carrier or present in the solution.

When the analyte is an antibody, the same principles can be employed but, instead of the antibody in the above-described processes, there must be used an antigen or an antibody directed against the antibody.

In immunological processes for the detection of an analyte, the detection of the hydrolase conjugate according to the process of the present invention is followed by the evaluation. From the presence of or, in the case of quantitative evaluation, the amount of the hydrolase conjugate to be detected, there can be deduced the presence or the amount of the analyte in the sample originally used. This can take place, for example, via a calibration curve.

Furthermore, the process according to the present invention can be used for the detection of a substance with hydrolase activity in a process for the detection of nucleic acids. Such processes are known to the expert in the field of nucleic acid hybridization tests. In these tests, single-stranded or double-stranded nucleic acids, especially DNA or RNA or fragments thereof, which are bound with a hydrolase as enzyme labelling are detected, the amount of which is a measure for the concentration of the nucleic acid to be detected. The detection of these hydrolase-labelled nucleic acids takes place in an advantageous way by the process according to the present invention for the detection of a substance with hydrolase activity.

The advantages of this new immunological process and of the new process for the detection of nucleic acids are given from the advantages of the process according to the present invention for the detection of substances with hydrolase activity.

The present invention also provides an agent for the detection of substances with hydrolase activity which contains at least one compound of general formula (I). Such an agent can be used for the detection-of substances with hydrolase activity in a sample to which an oxidation agent is added in a preceding, simultaneous or subsequent step.

An agent for the detection of substances with hydrolase activity is preferred which contains at least one compound of general formula (I) and an oxidation agent.

Furthermore, the agent can contain additives which admittedly are not necessary for the actual detection reaction but which exert an advantageous action. These include especially pH buffer substances which permit the detection reaction to be carried out at a constant pH value. Also included are wetting agents which bring about a uniform wetting of carrier materials and detergents.

The agent according to the present invention preferably contains one or more swellable or absorbent carriers. Such carriers are, for example, fleece or films, fleece being preferred. Sponge-like or porous carriers can also be used.

This agent preferably contains one or more swellable or absorbent carriers to which the hydrolase substrate and the oxidation agent are impregnated together or separately or they are incorporated in the case of films. Such agents are produced according to known processes.

Apart from the hydrolase substrate and the oxidation agent, as well as additives possibly present, the agent according to the present invention can also contain a solvent, the preferred solvent being water. Here, too, the hydrolase substrate and the oxidation agent can be present together or separately as solution.

The agent according to the present invention can also be present in the form of one or more powders or powder mixtures. Apart from the hydrolase substrate and the oxidation agent, such an agent can preferably also contain inert, soluble galenical filling materials, for example polyvinylpyrrolidone, polyethylene glycols and the like. The powder or powder mixture can also be pressed into tablets.

Such an agent can be used in a process for the detection of substances with hydrolase activity.

The present invention is also concerned with the use of compounds of general formula (I) in the above-described processes for the detection of substances with hydrolase activity in a sample.

The following Examples are given for the purpose of illustrating the present invention:

EXAMPLE 1

4-[(4-(4-Dimethylaminophenyl)-5-methyl)-1H-imidazol-2-yl]-2-methoxyphenol hydrochloride A solution of 30.4 g. (0.2 mole) 4-hydroxy-3-methoxybenzaldehyde (vanillin) in 400 ml. glacial acetic acid is heated under reflux for 3 hours with 38.24 g. (0.2 mole) 1-(4-dimethylaminophenyl)-propane-1,2-dione and 154 g. (2 mole) ammonium acetate and thereafter 1.1 liters of a concentrated aqueous solution of ammonia added thereto while cooling with ice. The crude product obtained is taken up in ethyl acetate, shaken up with water and, after drying over anhydrous sodium sulphate, the solvent is evaporated off under a vacuum. After dissolving the residue in ethanol, the hydrochloride is precipitated by the addition of 5N ethereal hydrochloric acid and this then purified by recrystallization from isopropanol/water (3:1 v/v). There are obtained 58 g. (81% of theory) of colorless crystals of the title compound; m.p. >200° C. (decomp.). MS: m/e=323 (base).

After oxidation of the leuko compound with hydrogen peroxide/peroxidase→chromogen $\lambda_{max}$. 693 nm, $\epsilon = 19500$.

TLC (silica gel, ethyl acetate) $R_f = 0.27$.

EXAMPLE 2

4-[(4-(4-Dimethylaminophenyl)-5-methyl)-oxazol-2-yl]-2-methoxyphenol a) 4-N,N-Dimethylamino-α-(4-hydroxy-3-methoxybenzoyloxy)-propiophenone 4.5 g. (0.024 mole) Sodium 4-hydroxy-3-methoxybenzoate are suspended in 50 ml. dimethylformamide, 8 g. (0.03 mole) 4-N,N-dimethylamino-α-bromopropiophenone are added thereto and the reaction mixture heated under reflux for 6 hours. After evaporation in a vacuum, the residue is chromatographed on a silica gel column (silica gel 60; 3 cm. diameter; 26 cm. filling height; elution agent: n-heptane/methyl ethyl ketone 2:1 v/v). There are obtained 3.5 g. (42.5% of theory) of the title compound; m.p. 151°-154° C.

b) 4-[4-(4-Dimethylaminophenyl)-5-methyloxazol-2-yl]-2-methoxyphenol

The product obtained in Example 2a) is heated under reflux for 3 hours under an atmosphere of argon with 4.2 g. (0.054 mole) ammonium acetate in 18 ml. glacial acetic acid. Upon cooling, there is obtained a beige-colored product which, after stirring with 50 ml. water, filtering off with suction and drying over phosphorus pentoxide, gives 3.1 g. (94.5% of theory) of the title compound; m.p. 170°-173° C.

TLC: (silica gel 60-F254; elution agent toluene:methanol 5:1 v/v); $R_f = 0.31$, MS: m/e 324. $\lambda_{max}$. 542 nm; $\epsilon = 14558$ after oxidation with hydrogen peroxide/peroxidase.

EXAMPLE 3

4-[4-(4-Dimethylaminophenyl)-5-methylthiazol-2-yl]-2,6-dimethoxyphenol a) 4-[4-(4-Dimethylaminophenyl)-5-methylthiazol-2-yl]-2,6-dimethoxyphenol benzyl ether 7.4 g. (0.024 mole) 4-Benzyloxy-3,5-dimethoxyphenylthioacetamide are dissolved in 240 ml. anhydrous ethanol, mixed with 6.2 g. (0.026 mole) 4-dimethylamino-α-bromopropiophenone and heated under reflux for 6 hours. After filtering off with suction and washing the reaction product with anhydrous ethanol, there are obtained 8.5 g. (76% of theory) of the benzyloxy compound in the form of yellow crystals; m.p. 50°-53° C. TLC (silica gel 60-F254; toluene/ethyl acetate 5:1 v/v)uniform.

b) 4-[4-(4-Dimethylaminophenyl)-5-methylthiazol-2-yl]-2,6-dimethoxyphenol

The O-benzyl ether obtained in Example 3a) is dissolved in 300 ml. methanol with warming and, while boiling under reflux, gaseous hydrogen chloride is passed in for 2 hours. Upon cooling, there are obtained 5.9 g. (88.2% of theory) of yellow crystals; m.p. 230°-233° C.; MS; m/e=370; $\lambda_{max}$. 564 nm, $\epsilon = 7687$ after oxidation with hydrogen peroxide/peroxidase.

EXAMPLE 4

4-[4-(4-Dimethylaminophenyl)-5-methyl-1H-imidazol-2-yl]-2-methoxyphenyl acetate 3.5 g. (0.01 mole) 4-[4-(4-dimethylaminophenyl)-5-methyl-1H-imidazol-2-yl]-2-methoxyphenol hydrochloride are dissolved in 200 ml. pyridine, 20 ml. acetic anhydride are added dropwise thereto, the reaction mixture is stirred for 1 hour at ambient temperature the crystals formed are filtered off with suction, the filter residue is washed with ice cold ethanol and the crystalline acetate obtained is dried at 400° C. in a drying cabinet. There are obtained 3.23 g. (82% of theory) of bright yellow crystals of the title compound; m.p. 253°-256° C.; MS: m/e 365.

TLC (silica gel 60 F 254; methylene chloride/methanol 5:1 v/v); $R_f = 0.77$.

The following compounds are prepared analogously:

EXAMPLE 4a

4-[4-(4-Dimethylaminophenyl)-5-methyloxazol-2-yl]-2-methoxyphenyl acetate.

MS: m/e=366; m.p. 97°-102° C.; yield 75% of theory. TLC (silica gel 60-F-254; toluene/methanol 5:1 v/v) $R_f = 0.36$

EXAMPLE 4b

4-[4-(4-Dimethylaminophenyl)-5-methylthiazol-2-yl]-2,6-dimethoxyphenyl acetate

MS: m/e=412; m.p. 247°–249° C.; yield 73% of theory. TLC (silica gel 60-F 254; toluene/ethyl acetate 5:1 v/v) $R_f$=0.34.

EXAMPLE 4c

4-[4-(4-Dimethylaminophenyl)-5-methyl-1H-imidazol-2-yl]-2,6-dimethoxyphenyl acetate MS: m/e=395; m.p.>250° C.; yield 78% of theory. TLC (silica gel 60-F 254; toluene/methanol 5:1 v/v) $R_f$=0.19

Enzymatic cleavage and subsequent oxidation with potassium ferricyanide→chromogen; $\lambda_{max}$. 680 nm, 1 g $\epsilon$=4.4.

EXAMPLE 4d

4-[4,5-Bis-(4-dimethylaminophenyl)-1H-imidazol-2-yl]-2,6-dimethoxyphenyl acetate MS: m/e=500; m.p. 261°–262° C.; yield 72% of theory. TLC (silica gel 60-F 254; chloroform/tetrahydrofuran 1:1 v/v): $R_f$=0.81.

Enzymatic cleavage and subsequent oxidation with potassium ferricyanide→chromogen: $\lambda_{max}$. 643, 1 g $\epsilon$=4.36.

EXAMPLE 5

4-[4-(4-Dimethylaminophenyl)-5-methyl-1H-imidazol-2-yl]-2-methoxyphenyl dodecanoate 1.6 g. (0.005 mole) 4-[4-(4-Dimethylaminophenyl)-5-methyl-1H-imidazol-2-yl]-2-methoxyphenol is dissolved in 20 ml. anhydrous pyridine and 3.6 ml. (0.01 mole) dodecanoyl chloride (98%) added dropwise thereto, while stirring, in the course of 10 minutes. After further stirring for 1 hour, 50 ml. ice water are added thereto, followed by extraction twice with, in each case, 50 ml. ethyl acetate. After drying over anhydrous sodium sulphate and evaporation of the solvent, the crude product obtained is purified by column chromatography (silica gel; toluene/ethyl acetate 1:1 v/v). There is obtained 1.3 g. (48% of theory) of the title compound in the form of beige-colored crystals. MS: m/e=505; m.p. 110°–112° C. TLC: (silica gel 60-F 254; toluene/methanol 5:1 v/v) $R_f$=0.34.

The following compounds are prepared analogously:

EXAMPLE 5a

4-[4-(4-Dimethylaminophenyl)-5-methyl-1H-imidazol-2-yl]-2-methoxyphenyl propanoate MS: m/e=379; m.p. 244°–246° C.; yield 56% of theory. TLC (silica gel 60-F 254; toluene/ethyl acetate 1:1 v/v) $R_f$=0.31.

EXAMPLE 5b

4-[4-(4-Dimethylaminophenyl)-5-methyl-1H-imidazol-2-yl]-2-methoxyphenyl butanoate MS: m/e=393; m.p. 62°–64° C.; yield 63% of theory. TLC (silica gel 60-F 254; toluene/ethyl acetate 1:1 v/v) $R_f$=0.33.

EXAMPLE 5c

4-[4-(4-Dimethylaminophenyl)-5-methyl-1H-imidazol-2-yl]-2-methoxyphenyl pentanoate MS: m/e=407; amorphous; yield 72% of theory. TLC (silica gel 60-F 254; toluene/ethyl acetate 2:1 V/V) $R_f$=0.18.

EXAMPLE 5d

4-[4-(4-Dimethylaminophenyl)-5-methyl-1H-imidazol-2yl]-2-methoxyphenyl octanoate.

MS: m/e=449; m.p. 126°–129° C.; yield 78% of theory. TLC (silica gel 60-F 254; toluene/ethyl acetate 1:1 v/v) $R_f$=0.44.

EXAMPLE 6

4-[4-(4-Dimethylaminophenyl)-5-methyl-1H-imidazol-2-yl]-2-methoxyphenyl dihydrogen phosphate To a mixture of 20 ml. pyridine and 6 ml. (0.065 mole) phosphorus oxychloride is added dropwise, within the course of 10 minutes, a solution of 3.2 g. (0.01 mole) 4-[4-(4-dimethylaminophenyl)-5-methyl-1H-imidazol-2-yl]-2-methoxyphenol in 20 ml. pyridine, the temperature thereby increasing to about 30° C. The reaction mixture is stirred for 3 hours at ambient temperature and, after standing for 12 hours at ambient temperature, the crystals formed are filtered off with suction, washed with water and the crude product dried over phosphorus pentoxide. Column chromatographic purification on silica gel 60 (column filling height 84 cm., diameter 2.5 cm.) with isopropanol/n-butyl acetate/water/ammonia 50:30:15:5 v/v/v/v gives 1.4 g. (24% of theory) of the title compound. MS: m/e=403; m.p. 226°–230° C. TLC (silica gel 60-F 254; n-propanol/ethyl acetate/water/acetic acid 60:10:30:5 v/v/v/v) $R_f$=0.51.

The following compounds are prepared analogously:

EXAMPLE 6a

4-[4-(4-Dimethylaminophenyl)-5-methyl-1H-imidazol-2-yl]-2,6-dimethoxyphenyl dihydrogen phosphate MS: m/e=433; m.p. 196°–198° C.; yield 35% of theory TLC (silica gel 60-F 254; methylene chloride/methanol 75:25v/v) uniform.

EXAMPLE 6b

4-[4-(4-Dimethylaminophenyl)-5-phenyl-1H-imidazol-2-yl]-2,6-dimethoxyphenyl dihydrogen phosphate MS: m/e=495; m.p. 230°–235° C.; yield 28% of theory; obtained from 4-[4-(4-dimethylaminophenyl)-5-phenyl-1H-imidazolyl]-2,6-dimethoxyphenol from the corresponding diketone analogously to Example 1.

MS: m/e=410; m.p. 181° C. (decomp.); $\lambda_{max}$. after oxidation with hydrogen peroxide/peroxidase 680 nm 0.1 g $\epsilon$=4.3.

EXAMPLE 6c

4-[4,5-Bis-(4-dimethylaminophenyl)-1H-imidazol-2-yl]-2,6-dimethoxyphenyl dihydrogen phosphate MS: m/e=538; m.p. 258°–260° C.; yield 45% of theory from 4-[4,5-bis-(4-dimethylaminophenyl)-1H-imidazol-2-yl]-2,6-dimethoxyphenol (Kodak)

$\lambda_{max}$. after oxidation with hydrogen peroxide/peroxidase 643 nm, 1 g $\epsilon$=4.4.

EXAMPLE 7

4-[4-(4-Dimethylaminophenyl)-5-methyl-oxazol-2-yl]-2-methoxyphenyl dihydrogen phosphate a) 4-[4-(4-Dimethylaminophenyl)-5-methyl-oxazol-2-yl]-2-methoxyphenyl dibenzyloxyphosphate 3.24 g. (0.01 mole) 4-[4-(4-Dimethylaminophenyl-5-methyl-oxazol-2-yl]-2-methoxyphenol are suspended in 40 ml. anhydrous tetrahydrofuran, 2 ml. carbon tetrachloride are added thereto and the reaction mixture is warmed in an oil bath to 40° C., the oxazole thereby substantially going into solution. Thereafter, there are successively added dropwise thereto 6 ml. dibenzyl phosphate and 4 ml. triethylamine within 5 minutes. The reaction mixture is stirred for 5 hours at ambient temperature, the triethylammonium chloride is filtered off with suction and the filtrate is evaporated in a vacuum. The crude product obtained is purified by column chromatography (silica gel 60, column 1.1 m. height, 3 cm. diameter; toluene/methanol 20:1 v/v).

b) 4-[4-(4-Dimethylaminophenyl)-5-methyl-oxazol-2-yl]-2-methoxyphenyl dihydrogen phosphate 1 g. of the compound from Example 7a) is hydrogenated in a mixture of 8 ml. methanol and 8 ml. dioxan, with the addition of 0.06 g. palladium oxide, for 4 hours at ambient temperature. Thereafter, the end product is purified by column chromatography to give 0.8 g. (19.8% of theory) of the title compound in the form of a yellow oil.

MS: m/e=404. amorphous.

TLC (silica gel 60-F 254; n-propanol/ethyl acetate/water/toluene/glacial acetic acid 60:10:30:5:2 v/v/v/v/v) $R_f$=0.74.

EXAMPLE 7a

4-[4,5-Bis-(4-dimethylaminophenyl)-oxazol-2-yl]-2,6-dimethoxyphenyl dihydrogen phosphate MS: m/e=539; m.p. 195°-200° C. from 4-[4,5-bis-(4-dimethylaminophenyl)-oxazol-2-yl]-2,6-dimethoxyphenol.

MS: m/e=459; m.p. 218° C.

$\lambda_{max}$ after oxidation with hydrogen peroxide/peroxidase 555 nm, 1 g $\epsilon$=3.85.

EXAMPLE 8

{4-[4-(4-Dimethylaminophenyl)-5-methyl-1H-imidazol-2-yl]-2-methoxyphenyl}-2-acetamido-2-deoxy-$\epsilon$-D-glucopyranoside a) 2-[4-(2-Acetamido-2-deoxy-3,4,6-triacetyl-$\beta$-D-glucopyranosyloxy)-3-methoxyphenyl]-5-methyl-4-(4-dimethylaminophenyl)-1,3-imidazole (MS=651)

To a solution of 7 g. (0.025 mole) n-butyltriethylammonium bromide in 200 ml. water is added a solution of 5.9 g. (0.0164 mole) 4-[4-(4-dimethylaminophenyl)-5-methyl-1H-imidazol-2-yl]-2-methoxyphenol in 200 ml. chloroform, as well as 14.2 g. (0.039 mole) 1-chloro-2-desoxy-2,3,4,6-tetraacetyl-$\epsilon$-D-glucosamine and 13.9 g. (0.102 mole) potassium carbonate. The reaction mixture is boiled under reflux for 4 hours with vigorous stirring. After cooling, the chloroform phase is separated off and the solvent evaporated in a vacuum. The crude product obtained is purified by column chromatography on silica gel (elution agent methylene chloride/methanol 1:1 v/v). There are obtained 4.4 g. (41.1% of theory) of the tetraacetyl compound.

b) {4-[4-(4-Dimethylaminophenyl)-5-methyl-1H-imidazol-2-yl]-2-methoxyphenyl}-2-acetamido-2-deoxy-$\beta$-D-glucopyranoside For the deacetylation of the product obtained in Example 8a), this is dissolved in 300 ml. methanol and, after the addition of 20 g. sodium hydrogen carbonate, stirred for 3 hours at 30° C. After filtering off the inorganic material with suction, the solvent is evaporated and the end product is then purified by column chromatography on silica gel 60 (elution agent toluene/methanol 1:1 v/v). There are obtained 3.1 g. (36% of theory) of TLC-uniform product which, after stirring with ice-cold methanol, gives 1.8 g. (21% of theory) of the title compound.

MS: m/e=525; m.p. 181° C. TLC (silica gel 60-F 254; toluene/ethyl acetate/methanol 1:1:1 v/v/v) $R_f$=0.21.

At pH 6 and pH 9, the compound is a very good substrate for N-acetyl-$\beta$-D-glucosaminidase (strong blue coloration).

EXAMPLE 9

2-(4-$\beta$-D-Galactopyranosyloxy-3-methoxyphenyl)-5-methyl-4-(4-dimethylaminophenyl)-1,3-imidazole a) 2-[4-(tetra-$\beta$-acetyl-p-D-galactopyranosyloxy)-3-methoxyphenyl]-5-methyl-4-(4-dimethylaminophenyl)-1,3-imidazole A solution of 4.8 g. (10 mmole) (4-formyl-2-methoxyphenyl)-2,3,4,6-tetra-O-acetyl-$\beta$-D-galactopyranoside (R. G. Price et al., Clin. Chim. Acta, 124, 195-204/1982), 1.9 g. (10 mMole) 1-(4-dimethylaminophenyl)-propane-1,2-dione and 7.7 g. (100 mmole) ammonium acetate in 200 ml. glacial acetic acid is heated to 125° C. for 1 hour. Subsequently, the reaction mixture is poured on to ice/water and the precipitate obtained is filtered off with suction and dried. After purification by column chromatography (silica gel; toluene-/ethyl acetate/methanol 4:4:1 v/v/v), there are obtained 4.2 g. (65% of theory) of the title compound; m.p. 163°-168° C., m/e 653 (M+).

b) 2-(4-$\beta$-D-galactopyranosyloxy-3-methoxyphenyl)-5-methyl-4-(4-dimethylaminophenyl)-1,3-imidazole 5 g. (7.6 mmole) of the compound obtained in Example 9a) in 30 ml. methanol is mixed at 0° C. with 5 ml. of a 1N solution of sodium methylate. After 3 hours, the solution is treated with a weakly acidic ion exchanger, for example Amberlite IRC 50, H+ form, filtered and the filtrate evaporated. The residue is digested with diethyl ether/petroleum ether and filtered off. Yield 2.7 g. (73% of theory); m.p. 140° C. (with foaming). MS (neg. FAB): m/e=484.

TLC (silica gel 60; isopropanol/methanol 1:1 v/v) $R_f$=0.4.

EXAMPLE 10

2-(4-$\beta$-D-galactopyranosyloxy-3-methoxyphenyl)-4,5-bis-(4-dimethylaminophenyl)-1,3-imidazole a) In the same way as in Example 9, 4.8 g. (10 mmole) (4-formyl-2-methoxyphenyl)-2,3,4,6-tetra-O-acetyl-$\beta$-D-galactopyranoside (R. G. Price et al., Clin. Chim. Acta, 124, 195-204/1982), 3 g. (10 mmole) 4,4'-bis-(dimethylamino)-benzil and 7.7 g. (100 mmole) ammonium a are reacted in 200 ml. glacial acetic acid. After boiling under reflux for 18 hours, working up and purifying by chromatography, there is obtained the tetra-O-acetylgalactosyl derivative; yield 4.7 g. (62% of theory).

b) For deacetylation, 1.26 g. (1.7 mmole) of the above-obtained compound is treated with a suspension of 1.7 g. sodium hydrogen carbonate in 150 ml. methanol for 2 hours at 40° C. After filtering off the inorganic precipitate, the filtrate is evaporated and the residue purified by chromatography (silica gel 60; toluene-/ethyl acetate/methanol 2:2:1 v/v/v); yield 0.77 g. (77% of theory); m.p. 174°–182° C.

EXAMPLE 11

In a manner analogous to that described in Example 10, the imidazole derivatives set out in the following are obtained in two reaction steps. In the first step, from the appropriate peracetylated (4-formylphenyl)-β-D-galactosides and the appropriate 1,2-diketones are prepared, by reaction with ammonium acetate in glacial acetic acid, the peracetylated galactosides which were deacetylated in the second reaction step.

a) 2-(4-β-D-Galactopyranosyloxyphenyl)-4-(4-dimethylaminophenyl)-5-methyl-1,3-imidazole from 4.5 g. (10 mmole) (4-formylphenyl)-2,3,4,6-tetra-O-acetyl-β-D-galactopyranoside (Z. Csuros et al., Acta Chim. Acad. Sci. Hung., 42, 263 267/1964) and 1.9 g. (10 mmole) 1-(4-dimethylaminophenyl)-propane-1,2-dione; reaction period 2 hours; tetra-O-acetyl-β-D-galactopyranoside; yield 4.6 g. (74% of theory).

Deacetylation analogously to Example 10b); yield 74% of theory; m.p. 177°–187° C.

b) 2-(4-β-D-Galactopyranosyloxyphenyl)-4,5-bis-(4-dimethylaminophenyl)-1,3-imidazole from 4.5 g. (10 mmole) (4-formylphenyl)-2,3,4,6-tetra-O-acetyl-β-D-galactopyranoside (Z. Csuros et al., Acta Chim. Acad. Sci. Hung.,.42, 263–267/1964) and 3 g. (10 mmole) 4,4'-bis-(dimethylamino)-benzil; reaction period 2 hours; tetra-O-acetyl-β-D-galactopyranoside; yield 2.2 g. (30% of theory).

Deacetylation analogously to Example 10 b); yield 83% of theory; m.p. 230°–237° C.

c) 2-(3-Chloro-4-0-D-galactopyranosyloxyphenyl)-5-methyl-4-(4-dimethylaminophenyl)-1,3-imidazole from 4.9 g. (10 mmole) (2-chloro-4-formylphenyl)-2,3,4,6-tetra-O-acetyl-β-D-galactopyranoside (prepared from 2,3,4,6-tetra-O-acetyl-α-D-galactopyranosyl bromide and 2-chloro-4-formylphenol according to the procedure of R. G. Price et al., Clin. Chim. Acta, 124, 195–204/1982) and 1.9 g. (10 mmole) 1-(4-dimethylaminophenyl)-propane-1,2-dione; reaction period 2 hours, tetra-O-acetyl-β-D-galactopyranoside; yield 5.95 g. (90% of theory).

Deacetylation analogously to Example 10 b).

d) 2-(3-Chloro-4-β-D-galactopyranosyloxyphenyl)-4,5-bis-(4-dimethylaminophenyl)-1,3-imidazole from 4.4 g. (9 mmole) (2-chloro-4-formylphenyl)-2,3,4,6-tetra-O-acetyl-β-D-galactopyranoside (prepared from 2,3,4,6-tetra-O-acetyl-α-D-galactopyranosyl bromide and 2-chloro-4-formylphenol according to the procedure of R. G. Price et al., Clin. Chim. Acta, 124, 195–204/1982) and 2.7 g. (9 mmole) 4,4'-bis-(dimethylamino)-benzil; reaction period 6 hours; tetra-O-acetyl-β-D-galactopyranoside; yield 6.9 g. of crude product which, without chromatographic purification, was subjected to deacetylation analogously to Example 10 b).

EXAMPLE 12

2-(4-β-D-Galactopyranosyloxy-3-methoxyphenyl)-4,5-bis-(4-methoxyphenyl)-I,3-imidazole a) 2-14-(Tetra-O-acetyl-β-D-galactopyranosy-3-methoxyphenyl]-4,5-bis-(4-methoxyphenyl)-1,3-imidazole A solution of 14 g. (29 mmole) vanillin 2,3,4,6-tetra-O-acetyl-β-D-galactopyranoside (Price et al., loc. cit.), 7.8 g. (29 mMole) 4,4'-dimethoxybenzil and 13.2 g. (174 mmole) ammonium acetate in 700 ml. glacial acetic acid is boiled under reflux for 5 hours while stirring and under a protective gas atmosphere. Subsequently, the reaction mixture is allowed to cool to 20° C. and the acetic acid is evaporated off under a vacuum with the repeated addition of toluene. The crude product is used in the next step without further purification. TLC (silica gel 60, elution agent ethyl acetate/petroleum ether 1:1 v/v): $R_f = 0.1$.

b) 2-(4-β-D-galactopyranosyloxy-3-methoxyphenyl)-4,5-bis-(4-methoxyphenyl)-1,3-imidazole The crude product obtained in a) is suspended in 300 ml. anhydrous methanol and mixed with an amount of saturated methanolic sodium methylate solution sufficient to give a pH value of 12 to 13. The reaction mixture is stirred at 20° C. for about 1 hour until deacetylation is complete (TLC monitoring, pH control) and the solution is neutralized by the addition of an acidic ion exchanger (Dowex 50 WX 8, H+). After 15 minutes, the ion exchanger is filtered off and the filtrate is evaporated in a vacuum. Purification takes place by flash chromatography on silica gel (elution agent: ethyl acetate/methanol 7:3 v/v). TLC (silica gel 60, elution agent ethyl acetate/methanol 7:3 v/v): $R_f = 0.4$. Yield 4.9 g. (30% of theory). MS (neg. FAB): m/e=563.

EXAMPLE 13

2-(4-β-D-Galactopyranosyloxy-3-methoxyphenyl)-4,5-bis-(4-methylphenyl)-1,3-imidazole The corresponding galactoside was prepared with 4,4'-dimethylbenzil analogously to Example 12. TLC (silica gel 60, elution agent ethyl acetate/methanol 73 v/v): $R_f = 0.5$. MS (neg. FAB): m/e=531.

EXAMPLE 14

Suitability as hydrolase substrates

In a spot test, there was investigated the hydrolysis of various compounds by appropriate hydrolases (aryl sulphatase, acidic and alkaline phosphatase, esterase, acetyl-β-O-glucosamidase and lipase). The base thereby liberated was simultaneously oxidized by potassium ferricyanide to the colored material and the color formation evaluated visually.

Carrying out/results

The rate of hydrolysis was evaluated visually at pH 6.0, as well as at pH 9.0, by spotting a hydrolase solution on to a substrate-buffer-oxidation agent-paper. The enzyme concentration was about 1000 U/ml. and the test temperature was ambient temperature. The non-enzymatic hydrolysis with a 0.9% aqueous sodium chloride solution as sample was evaluated for the purpose of comparison. By the use of the corresponding free base, the oxidizability with potassium ferricyanide was demonstrated.

PRODUCTION OF THE SUBSTRATE PAPERS

Fleece 6.0

Impregnation solution: 100 mmole/liter potassium dihydrogen phosphate 10 mmole/liter potassium ferricyanide 2% Pluronic ® F 68

The pH value was adjusted to 6.0 with a 2N aqueous solution of potassium hydroxide.

Fleece pH 9.0

Impregnation solution: 100 mmole/liter glycine 10 mmole/liter potassium ferricyanide 2% Pluronic ® 68

The pH value was adjusted to 9.0 with a 2N aqueous solution of sodium hydroxide.

Impregnation: An 8×30 cm. paper fleece (Whatman 3M) was impregnated with 8 ml. of impregnation solution and dried for 30 minutes at 50° C. in a drying cabinet.

The so impregnated buffer-oxidation agent papers were cut up into 8×2 cm. strips and post-impregnated with substrate solution. Substrate solution/impregnation solution: 5 mg. of the substrate to be tested (or the free base) were dissolved or suspended in 1 ml. methanol and, in each case, 10 μl. thereof applied to the buffer-oxidation agent papers. The solvent was evaporated with a blow drier. On to this substrate oxidation agent surface were then dosed on the hydrolase solutions and evaluated. The compounds described in Examples 4 to 8 showed positive results on the above-described papers. The results obtained are set out in the following Table:

TABLE

| Example | enzyme | pH 6 | pH 9 |
| --- | --- | --- | --- |
| 4 | 1 | + + | + + + |
| 4a | 1 | + + + | + + + |
| 4b | 1 | + | + + |
| 4c | 1 | + + + | + + + |
| 4d | 1 | + + | + + |
| 5 | 1 | + | + + |
| 5a | 1 | + | + + |
| 5b | 1 or 4 | + + | + + + |
| 5c | 1 | + + | + + |
| 5d | 1 | + + | + + + |
| 6 | 2 | — | + + |
| 6a | 2 | — | + + + |
| 6b | 2 | + + | + + + |
| 6c | 2 | + | + + |
| 7b | 2 | + | + + |
| 7c | 2 | + + | + + + |
| 8 | 3 | + + + | + + + |

Enzyme
1 esterase from hog's liver
2 alkaline phosphatase
3 N-acetyl-β-D-glucosaminidase
4 lipase
Coloration
+ coloration
+ + strong coloration
+ + + strong and rapid coloration.

EXAMPLE 15

Figure 1:
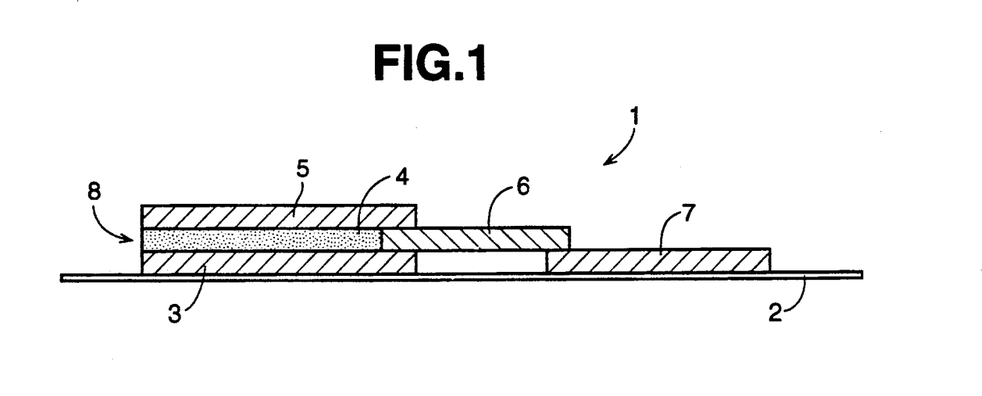
FIG. 1 is a test apparatus which can be used in the practice of the invention.

Detection of human chorionic gonadotropin (hCG) in a sample a) Production of a test carrier 1 (FIG. 1)

A piece of paper (Type 4210 of the firm Kalff) was cut up into strips (2.6 cm. long and 0.6 cm. wide). 20 μl. of a solution of 40 mg./ml. 2-(4-β-D-galactopyranosyloxy-3-methoxyphenyl)-4,5-bis(4-methoxyphenyl)-1,3-imidazole (galactosidase substrate from Example 12) in dimethyl sulphoxide were mixed with 20 μl. of a 24% solution of polyvinyl alcohol in water. This mixture was applied to the middle of the paper strip.

b) Production of fleece 5

A piece of paper (Type 4210 of the firm Kalff) was cut up into strips (2.6 cm. long and 0.6 cm. wide). One end was impregnated with 100 μl. phosphate-buffered saline (pH 7.0), 1% bovine serum albumin and 0.1% Tween ® 20. On the middle of the strip was applied 7.5 μl. of a solution which contained 20 U/ml. of a conjugate of a Fab fragment of a monoclonal antibody against hCG and β-galactosidase (substance with galactosidase activity), 100 μg./ml. of a monoclonal mouse antibody against the β chain of hCG and 7.5 mg./ml. 4-aminobenzyl-1-thio-o-D-galactopyranoside. The end which lies opposite to the buffer-impregnated end was impregnated with 10 μl. of a 5% solution of polyvinyl alcohol in water.

c) Production of fleece 6

On a piece of paper (Type 3512 of the firm Schleicher & Schull) was fixed, after activation with cyanogen bromide, sheep antibody against the Fc part of mouse antibodies. A piece of this material was cut up into a strip (length 1.1 cm. and width 0.6 cm.).

d) Production of fleece 7

A piece of paper (Type D-28 of the firm Whatman) was cut up into a size of 5×0.6 cm.

e) Fleece 3 and 5 are separated from one another by a plastic film 4.

By sticking the dried fleece on to a base film 2 with a width of 0.6 cm., there was produced the test carrier 1 illustrated in FIG. 1 of the accompanying drawings. Fleece 5 is thereby stuck on in such a manner that the end impregnated with polyvinyl alcohol points in the direction of the end 8 of the test carrier.

B) Carrying out of the test a) Sample preparation 0.5 ml. of sample was mixed with 0.5 ml. of a solution which contains 4 mmole/liter sodium perborate and 10 mg./liter horseradish peroxidase (oxidation agent) in phosphate buffer (pH 7).

b) Application of the sample to the test strip

The end 8 of the test strip 1 was placed in the solution. The hCG-containing solution penetrated into the fleece 5 and fleece 3 and dissolved the substances present thereon. By reaction of hCG with the β-galactosidase-labelled Fab fragment and the monoclonal antibody against the β-chain of hCG, in the solution in fleece 5 there is formed a β-galactosidase-labelled immune complex of the three components. This immune complex, which in this case represents the substance with hydrolase activity, is now detected in fleece 6 by means of the process according to the present invention. The solution with the immune complex penetrates just like the solution with the substrate from fleece 3 into fleece 6 and is there mixed with this substrate solution. In fleece 6, the immune complex formed, as well as the excess of the monoclonal antibody against the β-chain of hCG, is bound to fleece 6 via the fixed sheep antibody. A possible excess of β-galactosidase-labelled Fab fragment flows further into fleece 7. Due to the β-galactosidase labelling of the bound immune complex and with the help of the oxidation agent, within 10 minutes there is formed a red color in fleece 6.

If no hCG was contained in the sample, then β-galactosidase-labelled immune complex also could not be formed. Therefore, no substance with hydrolase activity is bound in fleece 6 and thus no color development has taken place. On the other hand, the total amount of β-galactosidase-labelled Fab fragment is still contained in the solution, which penetrates into fleece 7. Therefore, a color development takes place in fleece 7 which results from the reaction of the β-galactosidase-labelled Fab fragment which is also a substance with hydrolase activity. Thus, a control of the test takes place in that the process according to the present invention is also carried out in fleece 7. This is especially important in the case in which no hCG was present in the sample.

The evaluation can also take place quantitatively since the more hCG is present in the sample and thus the more bound β-galactosidase-labelled immune complex is present in fleece 6, the more intensive becomes the coloring of the fleece 6 after the expiry of 10 minutes.

EXAMPLE 16

Detection of thyroxine (T4)

A) Production of a test strip 11 (FIG. 2)
a) Fleece 14

Figure 2:
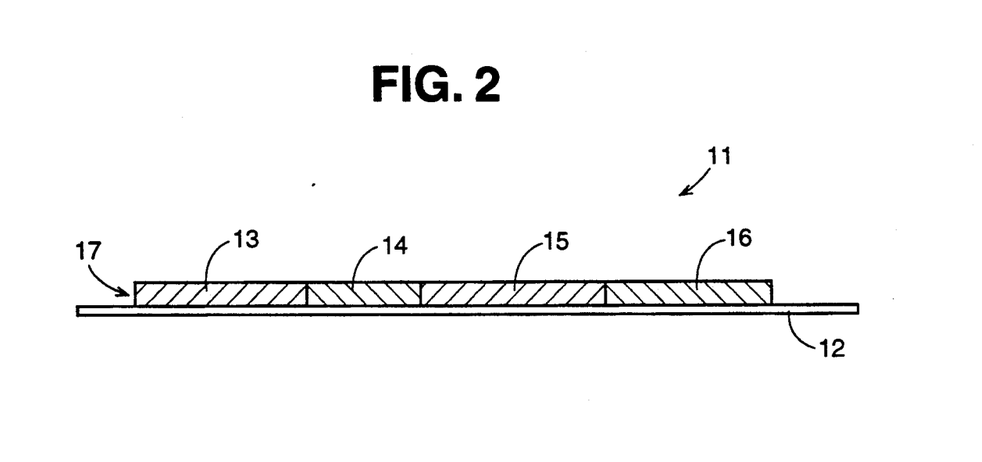
FIG. 2 is another test apparatus which can be used in the practice of the invention.

Fleece 14 is impregnated with a conjugate of β-galactosidase with an antibody against T4.

b) Fleece 15.

A piece of paper (Schleicher & Schüll 3512) was activated with cyanogen bromide and T4 succinimide ester bound thereon.

c) Fleece 16

Fleece 16 is a fleece which has been impregnated with 2-(4-β-D-galactopyranosyloxy-3-methoxyphenyl)-4,5-bis(4-methoxyphenyl)-1,3-imidazole (Example 12).

d) Fleece 13 serves for the sample application.

For the production of the test carrier 11, the fleece are fixed to a base film 12 as shown in FIG. 2 of the accompanying drawings.

B) Carrying out of the test
a) Sample preparation

The sample was prepared analogously to Example 15.

b) Carrying out

The test strip 11 was placed with the end 17 in the solution. The T4-containing sample penetrates into the fleece 13. From there, it flows on into fleece 14 from where it dissolves off the β-galactosidase conjugate. By immune reaction of the antibody with T4, there is formed a β-galactosidase-labelled immune complex. The solution which now, besides this immune complex, also contains an excess of the β-galactosidase conjugate, penetrates into fleece 15. This excess is there bound to the paper via bound T4.

The solution which still contains the immune complex penetrates into fleece 16. The process according to the invention for the detection of the β-galactosidase labelled immune complex, which represents the substance with hydrolase activity, there takes place. The more of this complex and thus also the more of T4 was present in the solution, the more strongly has the fleece 16 become red colored after 10 minutes. In the case of the absence of T4, the fleece 16 remains white.

Various embodiments of the compounds, compositions, devices and methods described and claimed herein will of course be evident to the skilled artisan. The examples given herein are in no way to be construed as limitative of the broad disclosure.

While there have been described what are at present considered to be the preferred embodiments of this invention, it will be obvious to one skilled in the art that various changes and modifications may be made therein without departing from the invention, and it is, therefore, aimed to cover all such changes and modifications as fall within the true spirit and scope of the invention.

What is claimed is:

1. In a process for the detection of hydrolase activity on an absorbent or swellable carrier by mixing (a) a hydrolase-containing sample with a hydrolase substrate which is cleavable by the hydrolase, with consumption of water, into a chromogenic compound and (b) an oxidation agent capable of oxidizing said chromogenic compound to effect a color change and then relating the resultant color change to hydrolase activity, the improvement which comprises employing as the hydrolase substrate at a pH of from 5 to 11, a compound of the formula wherein each of $R^1$, $R^2$ and $R^3$ is $C_1$–$C_4$ alkyl, or phenyl optionally substituted in the meta- or para- position by $C_1$–$C_6$ alkyl, $C_1$–$C_6$ alkoxy or mono- or di-($C_1$–$C_6$)-alkylamino, or optionally substituted by an O—X group in which X is a glycosyl, phosphate or acyl moiety of a natural substrate of the corresponding glycosidase, phosphatase or esterase, with the proviso that one of $R^1$, $R^2$ and $R^3$ is phenyl as set forth above which is substituted by a O—X group as set forth above and that another or both others of $R^1$, $R^2$ and $R^3$ is phenyl as set forth above without an O—X group, whereby glycosidase activity is detected when X is the glycosyl moiety, phosphatase activity is detected when X is the phosphate moiety or esterase activity is detected when is the acyl moiety.

2. A process according to claim 1 wherein X is a glycosyl radical selected from the group consisting of mono-, oligo- and polysaccharide radicals of the hexosepyranoside series.

3. A process according to claim 1 wherein X is a saturated or unsaturated acyl or aminoacyl radical having up to 20 carbon atoms.

4. A process according to claim 1 wherein X is a —$PO_3H_2$ radical, or an alkali metal, alkaline earth metal or ammonium salt thereof.

5. A process according to claim 1 in which the color change related to hydrolase activity is visually detected.

6. A process according to claim 2 in which the compound is {4-[4-(4-dimethylaminophenyl)-5-methyl-1H-imidazol-2-yl]-2-methoxyphenyl}-2-acetamido-2-deoxy-β-D-glucopyranoside.

7. A process according to claim 2 in which the compound is 2-(4-β-D-galactopyranosyloxy-3-methoxyphenyl)-5-methyl-4-(4-dimethylaminophenyl)-1,3-imidazole.

8. A process according to claim 2 in which the compound is 2-(4-β-D-galactopyranosyloxy-3-methoxyphenyl)-4,5-bis-(4-dimethylaminophenyl)-1,3-imidazole.

9. A process according to claim 2 in which the compound is 2-(4-β-d-Galactopyranosyloxyphenyl)-4-(4-dimethylaminophenyl)-5-methyl-1,3-imidazole.

10. A process according to claim 2 in which the compound is 2-(4-β-D-galactopyranosyloxyphenyl)-4,5-bis-(4-dimethylaminophenyl)-1,3-imidazole.

11. A process according to claim 2 in which the compound is 2-(3-chloro-4-β-D-galactopyranosyloxyphenyl)-5-methyl-4-(4-dimethylaminophenyl)-1,3-imidazole.

12. A process according to claim 2 in which the compound is 2-(3-chloro-4-β-D-galactopyranosyloxyphenyl)-4,5-bis-(4-dimethylaminophenyl)-1,3-imidazole.

13. A process according to claim 2 in which the compound is 2-(4-β-D-Galactopyranosyloxy-3-methoxyphenyl)-4,5-bis-(4-methoxyphenyl)-1,3-imidazole.

14. A process according to claim 2 in which the compound is 2-(4-β-D-galactopyranosyloxy-3-methoxyphenyl)-4,5-bis-(4-methylphenyl)-1,3-imidazole.

15. A process according to claim 3 in which the compound is 4-[4-(4-dimethylaminophenyl)-5-methyl-1H-imidazol-2-yl]-2-methoxyphenyl acetate.

16. A process according to claim 3 in which the compound is 4-[4-(4-dimethylaminophenyl)-5-methyl-1H-imidazol-2-yl]-2,6-dimethoxyphenyl acetate.

17. A process according to claim 3 in which the compound is 4-[4,5-bis-(4-dimethylaminophenyl)-1H-imidazol-2-yl]-2,6-dimethoxyphenyl acetate.

18. A process according to claim 3 in which the compound is 4-[4-(4-dimethylaminophenyl)-5-methyl-1H-imidazol-2-yl]-2-methoxyphenyl dodecanoate.

19. A process according to claim 3 in which the compound is 4-[4-(4-dimethylaminophenyl)-5-methyl-1H-imidazol-2-yl]-2-methoxyphenyl propanoate.

20. A process according to claim 3 in which the compound is 4-[4-(4-dimethylaminophenyl)-5-methyl-1H-imidazol-2-yl]-2-methoxyphenyl butanoate.

21. A process according to claim 3 in which the compound is 4-[4-(4-dimethylaminophenyl)-5-methyl-1H-imidazol-2-yl]-2-methoxyphenyl pentanoate.

22. A process according to claim 4 in which the compound is 4-[4-(4-dimethylaminophenyl)-5-methyl-1H-imidazol-2-yl-2-methoxyphenyl octanoate.

23. A process according to claim 4 in which the compound is 4-[4-(4-dimethylaminophenyl)-5-methyl-1H-imidazol-2-yl]-2-methoxyphenyl dihydrogen phosphate.

24. A process according to claim 4 in which the compound is 4-[4-(4-dimethylaminophenyl)-5-methyl-1H-imidazol-2-yl]-2,6-dimethoxyphenyl dihydrogen phosphate.

25. A process according to claim 4 in which the compound is 4-[4-(4-dimethylaminophenyl)-5-phenyl-1H-imidazol-2-yl]-2,6-dimethoxyphenyl dihydrogen phosphate.

26. A process according to claim 4 in which the compound is 4-[4,5-bis-(4-dimethylaminophenyl)-1H-imidazol-2-yl]-2,6-dimethoxyphenyl dihydrogen phosphate.

* * * * *